(12) United States Patent
Kabara

(10) Patent No.: US 6,638,978 B1
(45) Date of Patent: Oct. 28, 2003

(54) ANTIMICROBIAL PRESERVATIVE COMPOSITIONS AND METHODS

(76) Inventor: Jon J. Kabara, 2088 Riverwood, Okemos, MI (US) 48864

( * ) Notice: Subject to any disclaimer, the term of this patent is extended or adjusted under 35 U.S.C. 154(b) by 0 days.

(21) Appl. No.: 08/186,824

(22) Filed: Jan. 26, 1994

Related U.S. Application Data

(63) Continuation of application No. 07/971,665, filed on Nov. 4, 1992, now abandoned, which is a continuation of application No. 07/842,790, filed on Feb. 26, 1992, now abandoned, which is a continuation of application No. 07/431,671, filed on Nov. 2, 1989, now abandoned, which is a continuation of application No. 07/223,715, filed on Jul. 21, 1988, now abandoned, which is a continuation of application No. 06/854,155, filed on Apr. 21, 1986, now abandoned.

(51) Int. Cl.$^7$ .......................... A61K 31/22; A61K 37/23

(52) U.S. Cl. ........................ 514/550; 514/552; 514/946

(58) Field of Search ................................ 514/550, 552, 514/946

(56) References Cited

U.S. PATENT DOCUMENTS

| | | | |
|---|---|---|---|
| 1,772,975 A | | 8/1930 | Wieland |
| 2,154,449 A | | 4/1939 | Hoffman |
| 2,190,714 A | | 2/1940 | Hoffman |
| 2,466,663 A | | 4/1949 | Russ |
| 2,729,586 A | | 1/1956 | Peck |
| 2,752,284 A | | 6/1956 | Berliner et al. .............. 167/58 |
| 3,404,987 A | | 10/1968 | Kooistra |
| 3,959,491 A | | 5/1976 | Young et al. ............... 424/359 |
| 4,002,775 A | | 1/1977 | Kabara |
| 4,067,997 A | * | 1/1978 | Kabara ........................ 424/49 |
| 4,156,719 A | * | 5/1979 | Sezaki et al. ............... 424/118 |
| 4,160,820 A | * | 7/1979 | Wagenknecht ............... 424/48 |
| 4,187,286 A | | 2/1980 | Marcus ........................ 424/44 |
| 4,242,359 A | | 12/1980 | Cooper et al. ............... 424/250 |
| 4,247,552 A | | 1/1981 | Hallesy et al. .............. 424/325 |
| 4,277,461 A | | 7/1981 | Lucker et al. ................. 424/44 |
| 4,277,475 A | | 7/1981 | Vickery ....................... 424/250 |
| 4,298,624 A | | 11/1981 | Mehring et al. ............. 426/532 |
| 4,299,826 A | * | 11/1981 | Luedders ..................... 514/859 |
| 4,322,399 A | | 3/1982 | Ahmad et al. ................. 424/44 |
| 4,335,115 A | * | 6/1982 | Thompson et al. ......... 514/859 |
| 4,343,788 A | | 8/1982 | Mustacich et al. |
| 4,343,798 A | | 8/1982 | Fawzi |
| 4,360,013 A | | 11/1982 | Barrows ..................... 128/130 |
| 4,368,186 A | | 1/1983 | Vickery et al. ............... 424/78 |
| 4,371,518 A | | 2/1983 | Gazzani ....................... 424/78 |
| 4,392,848 A | | 7/1983 | Lucas et al. |
| 4,406,884 A | | 9/1983 | Fawzi et al. |
| 4,439,441 A | | 3/1984 | Hallesy et al. .............. 424/273 |
| 4,476,141 A | | 10/1984 | Cormier ..................... 424/321 |
| 4,551,148 A | | 11/1985 | Riley, Jr. et al. ............ 604/890 |
| 4,557,935 A | * | 12/1985 | af Ekenstam et al. ....... 424/130 |
| 4,722,941 A | | 2/1988 | Eckert et al. ................ 514/784 |
| 5,093,140 A | | 3/1992 | Watanabe ................... 426/326 |

FOREIGN PATENT DOCUMENTS

| | | | | |
|---|---|---|---|---|
| CH | 0634749 | * | 2/1983 | .......... A61K/47/00 |
| DE | 0143245 A2 | | 6/1985 | .......... C07C/69/30 |
| DE | 0161425 A2 | | 11/1985 | .......... A01N/47/44 |
| GB | 1481961 | | 8/1977 | |
| SE | 0634749 | * | 2/1983 | ................. 514/946 |

OTHER PUBLICATIONS

Kabara, J., *Medium–chain Fatty Acids and Esters as Antimicrobial Agents*, Cosmetic and Drug Preservation, pp. 275–304, 1984.

Kabara, J., *Toxicological, Bactericidal and Fungicidal Properties of Fatty Acids and Some Derivatives*, The Journal of the American Oil Chemist's Society, vol. 56, No. 11, pp. 760A–767A, 1979.

Kabara, J., *Inhibition of Staphylococlus Aureus in a Model Agar–Meat System By Monolaurin: A Research Note*, Journal of Food Safety, vol. 6, pp. 197–201, 1984.

Richard L. Boddie and Stephen C. Nickerson, *Efficacy of a Fatty Acid–Lactic Acid Postmilking Teat Cermicide in Reducing Incidence of Bovine Mastitis*, Oct., 1988, pp. 799–802.

*Before & After Pre–Milking and Post–Milking Teat Dip*, Diversey Wyandotte Corporation Brochure 1980.

Prince, H. N., "Effect of pH on the Antifungal Activity of Undecylenic Acid and its Calcium Salt," New Jersey (1959).

C. Nieman, "Influence of Trace Amounts of Fatty Acids on the Growth of Microorganisms," *Bacteriol. Rev.*, 18:147–163 (1954).

F.W. Chattaway and C. C. Thompson, "The Action of Inhibitors on Dermatophytes," *Biochem. J.*, 63:648–656 (1956).

(List continued on next page.)

*Primary Examiner*—Russell Travers
(74) *Attorney, Agent, or Firm*—Harness, Dickey & Pierce, P.L.C.

(57) ABSTRACT

The present invention discloses an antimicrobial preservative composition and methods of using the same. The antimicrobial preservative composition includes a glycerol fatty acid ester, a binary mixture of fatty acids including a first fatty acid antimicrobial agent selected from fatty acids having about six to about eighteen carbon atoms and a second fatty acid antimicrobial agent selected from fatty acids having about six to about eighteen carbon atoms where the second fatty acid is different from the first fatty acid and a food-grade carrier. Also disclosed is an antimicrobial preservative composition which includes a safe and effective amount of a ethoxylated or propoxylated glycerol fatty acid ester, a binary mixture of fatty acids including a first fatty acid antimicrobial agent selected from this $C_6$ to $C_{18}$ fatty acids and a second fatty acid antimicrobial agent selected from $C_6$ to $C_{18}$ fatty acids where the second fatty acid is different from the first fatty acid and a food-grade carrier. Further a method of preserving food compositions, cosmetics, drugs or the like to improve its shelf life is disclosed.

11 Claims, No Drawings

OTHER PUBLICATIONS

CA89(9):74466r, JP 53010141 (1978).
CA99(19):157083w, JP 58111669 (1983).
CA92(7):57080e, JP 54034061 (1979).
CA99(3):21158s, JP 58063357 (1983).
"Before & After™ Sanitizing Pre-milking and Post-milking Teat Dip," Diversey Wyandotte Corporation Brochure.
Satkowski, W.B., et al., "Polyoxyethylene Esters of Fatty Acids," Monsanto Company, St. Louis, Missouri, 5:142–174.
Kabara, J. "Cosmetic and Drug Preservation," Marcell Dekker, New York 275–304 (1984).
Kabara, J., *Antimicrobial Agents Derived From Fatty Acids*, JAOCS, vol. 61, No. 2, pp. 397–403, 1984.
Kabara. J., *GRAS Antimicrobia Agents for Cosmetic Products*, Journal of the Society of Cosmetic Chemists, vol. 31, pp. 1–10, 1980.
Schemmel, R., Lynch, P., Krohn, K., & Kabara, J., *Monolaurin as an Anticaries Agent*. 1966.
Kabara, J., Ohkawa, M., Ikekawa, T., Katori, T., & Mishikawa, Y., *Examination on Antitumor, Immunological and Plant–Growth Inhibitory Effects of Mongycerides of Caprylic, Capric, and Lauric Acids and Related Compounds*, Pharacological Effects of Lipids, vol. II, pp. 263–272, 1980, 1985.

Li, C., & Kabara, J., *Effects of Lauricidin on Fomes Annosus and Phellinus Werii*, AOCS Monograph No. 5, pp. 45–47, 1978.
Kenney, D., *Cosmetic Formulas Preserved With Food–Grade Chemicals*, Cosmetics and Toiletries, Part I, vol. 97, pp. 71–76, 1982.
Kabara, J., & Wernette, C., *Cosmetic Formulas Preserved with Food–Grade Chemicals*, Cosmetics and Toiletries, Part II, vol. 97, pp. 77–84, 1982.
Kabara, J., *A New Preservative System For Food*, Journal of Food Safety, vol. 4 pp. 13–25, 1982.
Branan, A., & Davison, P., *Antimicrobials in Foods*, Marcel Dekker, New York, 1983, pp. 109–140.
Kabara, J., *Fatty Acids and Derivatives as Antimicrobial Agents—A Review*, AOCS Monograph No. 5, pp. 1–14, 1978.
Schick, M.J., *Nonionic Surfactants*, Marcel Dekken, Inc., New York, 1966, Chap. 28, Sec. 13, pp. 958–960.
Dillan K., *Effects of the Ethylene Oxide Distribution on Nonionic Surfactant Properties*, JAOCS, vol. 62, No. 7, pp. 1144–1151, 1985.

* cited by examiner-

ANTIMICROBIAL PRESERVATIVE COMPOSITIONS AND METHODS

This is a continuation of U.S. patent application Ser. No. 07/971,665, filed Nov. 4, 1992 now abandoned which is a continuation of Ser. No. 07/842,790, filed Feb. 26, 1992 now abandoned which is a continuation of Ser. No. 07/431,671, filed Nov. 2, 1989 now abandoned which is a continuation of Ser. No. 07/223,715, filed Jul. 21, 1988 now abandoned which is a continuation of Ser. No. 06/854,155, filed Apr. 21, 1986 now abandoned.

TECHNICAL FIELD

The present invention relates generally to food grade materials as preservatives and, more particularly, to the addition of glyceryl fatty acid esters, in combination with at least one or more acids selected from the group consisting of $C_6$–$C_{18}$, preferably $C_6$–$C_{12}$, fatty acids to food compositions, cosmetics or pharmaceutical preparations or the like.

BACKGROUND OF THE INVENTION

The use of antimicrobial agents plays an important part in current food preservation techniques. However, the addition of these additives have several disadvantages. The addition of antimicrobials may dramatically effect the taste of the food composition. With certain additives, the amount of the additive which may be employed in a food composition may be limited by government regulations. And while many agents are useful in certain environments, certain additives may have a narrow spectrum of micro-organism activity and type of foods it may be employed with. Accordingly, there is a need for an antimicrobial that may be added to food compositions which is safe, effective and which overcomes these disadvantages. The present invention meets this need for food, cosmetic and drug preservation.

The prior art teaches several different carboxylic acids which are generally useful in suppressing the growth of fungi, bacteria, molds, and the like such as U.S. Pat. No. 2,154,449 issued to Hoffman et al. teaches the use of aliphatic $C_3$–$C_{12}$ carboxylic acids and their salts as mold inhibitors in food compositions. U.S. Pat. No. 2,190,714 issued to Hoffman, et al. teaches the addition of a $C_3$–$C_{12}$ carboxylic acid to inhibit growth food products other than margarine and sourdough bread. U.S. Pat. No. 3,404,987 to Kooistra, et al. teaches an antimicrobial containing edible mineral salt and edible acid preservative substances, particularly propionic acid. U.S. Pat. No. 2,466,663 issued to Russ, et al. teaches the use of a topical or intravenous caprylic acid solution to combat mycotic infections or growths. U.S. Pat. No. 2,729,586 issued to Peck teaches a therapeutic composition having at least one salt of a $C_3$–$C_{11}$ monocarboxylic acid and water soluble chlorophyll. However, the majority of these are outside the food area. For example, U.S. Pat. No. 4,406,884 issued to Fawzi discloses a topical antimicrobial composition in the form of an aqueous gel or lotion. This composition contains $C_5$–$C_{12}$ fatty acids having a pH no greater than about 5. U.S. Pat. No. 4,343,798 issued to Fawzi, teaches a topical antimicrobial anti-inflammatory composition having a pH no greater than about 5 and containing $C_5$–$C_{12}$ fatty acids together with a corticosteroid component. U.S. Pat. No. 4,489,097 issued to Stone, teaches the addition of anti-fungal/antibacterial materials to sterile compositions. The antifungal/antibacterial material disclosed is a $C_4$–$C_9$ carboxylate antimicrobial agent having a pH of about 6.0 or below. U.S. Pat. No. 4,410,442 issued to Lucas, et al. teaches solutions for use with hydrophilic soft contact lenses containing $C_5$–$C_{12}$ fatty acids, especially octanoic acid. U.S. Pat. No. 4,392,848 issued to Lucas, et al. teaches a catheter having a liquid reservoir of an antimicrobial agent flowing through the lumen of the catheter. The antimicrobial agent disclosed is a straight-chain carboxylic acid or carboxylic acid salt having a $C_4$–$C_9$ chain. U.S. Pat. No. 4,430,381 issued to Harvey, et al. teaches a process for imparting antimicrobial properties to a material. The antimicrobial being a $C_3$–$C_{12}$ alkane, alkene or alkyne monocarboxylate. U.S. Pat. Nos. 4,343,788 and 4,479,795, both issued to Mustacich, et al. teach medical polymers that provide diffusion for certain carboxylate antimicrobial agents. U.S. Pat. No. 4,002,775 issued to Kabara teaches a food grade microbicidal composition having a monoester with a $C_{12}$ aliphatic fatty acid as its primary microbicide. U.S. Pat. No. 1,772,975 issued to Weiland teaches the use of lactic acid, acetic acid, or combinations thereof, as antiseptics at properly adjusted pH levels.

Other materials also disclose the use of fatty acids for the suppression of fungi, bacteria, mold and the like. Kabara, J., *Medium-chain Fatty Acids and Esters as Antimicrobial Agents*, Cosmetic and Drug Preservation, Pgs. 275–304, 1984, teaches the use of $C_6$–$C_{22}$ saturated and unsaturated fatty acids as antimicrobials. Kabara, J., *Toxicological, Bactericidal and Fungicidal Properties of Fatty Acids and Some Derivatives*, The Journal of the American Oil Chemists' Society, Vol. 56, No. 11, Pages 760A–767A (1979) teaches the applying of fatty acids to animal skin and eyes. Some fatty acids were found to be skin and eye irritants. Kabara, J., *Inhibition of Staphylococlus Aureus In a Model Agar-Meat System By Monolaurin: A Research Note,* Journal of Food Safety, Vol. 6, Pgs. 197–201 (1984), teaches the use of monolaurin as a food preservative to combat microorganisms. Kabara, J., *Antimicrobial Agents Derives from Fatty Acids*, JAOCS, Vol. 61, No. 2, Pgs. 397–403 (1984) teaches the use of saturated and unsaturated fatty acids as antimicrobial agents. Kabara, J., *GRAS Antimicrobia Agents for Cosmetic Products,* Journal of the Society of Cosmetic Chemists, Vol. 31, Pgs. 1–10 (1980), teaches the composition of monolaurin, a phenol, di-tert-butyl anisole, and a chelating agent such as ethylenediaminetetracetic acid to be useful in destroying gram positive and gram negative bacteria. Schemmel, R., Lynch, P., Krohn, K., and Kabara, J., *Monolaurin as an Anticaries Agent,* teaches the use of glycerol-monolaurin in inhibiting development of smooth surface caries in rats innoculated with Streptococcus mutants. Kabara, Jr., Ohkawa M., Ikekawa, T., Katori, T., and Mishikawa, Y., *Examination on Antitumor, Immunological and Plant-Growth Inhiditory Effects of Monoglycerides of Caprylic, Capric, and Lauric Acids and Related Compounds,* Pharacological Effects of Lipids, Volume II, Pgs. 263–272 (1985) teaches the use of the monoglycerides or caprylic, capric and lauric acids for regulating antitumor, immunological, and plant-growth activity. Li, C., and Kabara, J., *Effects of Lauricidin on Fomes Annosus and Phellinus* Weirii, AOCS Monograph No. 5, Pgs. 45–47 (1978) teaches the use of monolaurin in combating root rot fungi in coniferous forest. Kenney, D., *Cosmetic Formulas Preserved With Food-Grade Chemicals,* Cosmetics and Toiletries, Part 1, Vol. 97, Pgs. 71–76 (1982) and Kabara, J. and Wernette, C., *Cosmetic Formulas Preserved with Food-Grade Chemicals,* Cosmetics and Toiletries, Part II, Vol. 97, Pgs. 77–84 (1982) teaches the use of monoglyceride emulsifier, food-grade phenols and a chelator in the preservation of cosmetics. Kabara, J., *A New Preservative System For Food,* Journal of Food Safety, Volume 4, Pgs. 13–25

(1982) teaches the use of monolaurin, a food grade phenolic, and a chelator as an antimicrobial for the preservation of food. Branan, A. and Davison, P. *Antimicrobials in Foods,* Marcel Dekker, New York 1983, Pgs. 109–140 teaches the use of saturated, unsaturated and esters of fatty acids as antimicrobials and the use of these compounds for food preservation. Kabara, J., *Fatty Acids and Derivatives as Antimicrobial Agents—A Review,* AOCS Monograph No. 5, Pgs. 1–14(1978) teaches the use of saturated, unsaturated and esters of fatty acids as antimicrobials and the use of these compounds for permeating microorganism cellular membranes for killing the microorganism.

The art also teaches many methods of ethoxalation. *Nonionic Surfactants,* Schick, M. J., Marcel Dekken, Inc., New York (1966) and Dillan, K. *Effects of the Ethylene Oxide Distribution on Nonionic Surfactant Properties,* JAOCS, Vol. 62, No. 7, Pgs. 1144–1151 (1985) teach the ethoxalation of primary alcohols to produce nonionic surfactants.

The above discussion clearly reflects the ambiguous state of the art with regard to the suitability and selection of fatty acid-based materials as food preservatives. The art disclosed materials vary widely in their preservative efficacy and in their spectrum of performance. (The term glyceryl and glycerol are used interchangeably here in when describing fatty acid esters.)

SUMMARY AND DETAILED DESCRIPTION OF THE INVENTION

The present invention relates to food and cosmetic compositions and methods of preservation. The present invention relates to the discovery that the spectrum and speed of activity of both modified and unmodified glyceryl fatty acid esters can be significantly improved when used in a mixture with one or more $C_6$–$C_{18}$ (preferably $C_6$–$C_{12}$) fatty acids. The present invention further relates to the additional discovery that the overall antimicrobial efficacy and acceptability of certain glyceryl fatty acid esters can be dramatically increased by the addition of certain ether groups, particularly ethoxy and propoxy units, either used alone or (when the ethoxylated or propoxylated glycerol fatty acid esters is) used in a trinary combination with a binary mixture of two or more $C_6$–$C_{18}$ (preferably $C_6$–$C_{12}$), fatty acids. Such materials provide effective antimicrobial activity and are accordingly useful in the preservation of food compositions, cosmetics, drugs, and the like where microbial organisms (including viruses) can decrease the shelf life or overall acceptability of the product.

In addition to being useful as pharmaceutical preservatives, the present invention has utility in topical pharmaceutical applications. The topical pharmaceutical applications are further discussed in my copending U.S. patent application entitled "TOPICAL ANTIMICROBIAL PHARMACEUTICAL COMPOSITIONS AND METHODS", Ser. No. 854,154, filed on the same day as the present application, incorporated herein by reference.

It has been observed that a combination of a glyceryl fatty acid ester and a mixture of at least one or more acids selected from the group consisting of fatty acids having from about six to about eighteen carbon atoms demonstrates remarkable preservative activity. However, other polyols such as polyglyceryl, sucrose, glucose, sorbitol, and the like sugar esters have been found to work satisfactorily when substituted for the glyceryl fatty acid ester. The useful glyceryl fatty acid esters include those selected from the groups consisting of glyceryl fatty acid esters having from about six to about twenty-one carbon atoms and fatty acids having from about six to about eighteen carbon atoms. The preferred glyceryl fatty acid ester compounds include monocaprylin, monocaprin, monolaurin, monomyristin, monopalmitolein, α-monopalmitin, monostearin, monoolein, 1-monolinolein, 1-monolinolenin, and mixtures thereof. Still more preferred compounds include monocaprylin, monocaprin, monolaurin, monomyristin, monopalmitolein, monoolein, monoicosenoin, and monoerucin and mixtures thereof. The highly preferred compounds include monocaprylin, monocaprin, and monolaurin and mixtures thereof. The preferred first and second fatty acid compounds for use in such combinations are straight chain materials having from about six to about twelve carbon atoms including caproic, heptanoic, caprylic, pelargonic, capric, undecanoic, lauric, myristic, palmitic, heptadecanoic and stearic. The most preferred are carproic, heptanoic, caprylic, capric, undecanoic, and lauric. Highly preferred materials include caproic, caprylic, and capric.

The glyceryl fatty acid esters, first fatty acid, and second fatty acid are added as a preservative to a food compositions, cosmetics, drugs or the like during mixing or manufacturing at a safe and effective level. In a preferred embodiment, they are present in the additive composition at a wt:wt ratio of ester: total fatty acids of about 1:10 to about 10:1; more preferably about 1:10 to about 1:1, and still more preferably about 1:5 to about 1:1 with the ester being present at a level of about 0.025 to 3%; more preferably about 0.025 to about 1%, and still more preferably about 0.05 to about 0.5% by weight of the preservative composition or the preserved composition.

It will be appreciated that the preferred levels described above relate to the preparation of an additive composition. The safe and effected level of such components as employed in the final preserved food, cosmetic, drug composition (or the like) vary according to a host of factors including the type of food, the base of the cosmetic, the mode of treatment of the drug, etc., the determination of the final level, i.e., the amount of the preservative composition to be added to the end product, is well within the skill of the artisan. In general, however, the additive composition of the present invention are added to the final product at a level of about 0.01 to about 10% to arrive at the preserved food compositions of the present inventions.

It has been further observed that a combination of a ethoxylated/propoxylated glyceryl fatty acid ester and a mixture of at least one or more acids selected from the group consisting of $C_6$–$C_{18}$, preferably $C_6$–$C_{12}$, fatty acids also demonstrates remarkable preservative activity. Also, other polyols such as polyglyceryl, sucrose, glucose, sorbitol, and the like sugar esters have been found to work satisfactorily when substituted for the glyceryl fatty acid ester. The useful glyceryl fatty acid esters include those selected from the groups consisting of glyceryl fatty acid esters having six to twenty-one, preferably six to fifteen, carbon atoms and fatty acids having six to eighteen carbon atoms. The preferred glyceryl fatty acid ester compounds include monocaprylin, monocaprin, monolaurin, monomyristin, monopalmitolein, α-monopalmitin, monostearin, monoolein, 1-monolinolein, 1-monolinolenin, and mixtures thereof. Still more preferred compounds include monocaprylin, monocaprin, monolaurin, monomyristin, monopalmitolein, monoolein, monoicosenoin, and monoerucin and mixtures thereof. The highly preferred compounds include monocaprylin, monocaprin, and monolaurin and mixtures thereof. These materials are modified by the addition of one or more ethoxy/propoxy units as described below prior to being employed in the combination. The preferred first and second fatty acid compounds for use in such combinations are straight chain materials having about six to about 14 carbon atoms including caproic, heptanoic, caprylic, pelargonic, capric, undecanoic, lauric, myristic, palmitic, heptadecanoic and stearic. The most preferred are carproic, heptanoic, caprylic, capric, undecanoic, and lauric. Highly preferred materials include caproic, caprylic, capric, and lauric.

The glyceryl fatty acid esters, first fatty acid, and second fatty acid are added as a preservative to a food composition, cosmetic, drug or the like during mixing or manufacturing. In a preferred embodiment, they are present in the additive composition at a wt:wt ratio of ester: total fatty acids of about 1:10 to about 10:1; more preferably about 1:10 to about 1:1, and still more preferably about 1:5 to about 1:1 with the ethoxylated/propoxylated glyceryl ester being present at a level of about 0.25 to about 3%; more preferably about 0.025 to about 1%; and still more preferably about 0.05% to about 0.5% by weight of the preservative composition or the preserved composition.

The glyceryl fatty acid esters may be ethoxylated or propoxylated under controlled conditions according to conventional methods, such as described below for use in the compositions and methods of the present invention.

It is well known that the ethoxylation or propoxylation of an antimicrobial agent generally renders that agent biologically inactive. See *Nonionic Surfactants,* Martin J. Schick, Marcel Dekker, Inc., New York, N.Y. Chap. 28, Pgs. 958–960.

Unexpectedly, it has been found that the addition of a limited number of ethoxy or propoxy units to a glyceryl fatty acid ester results in an antimicrobial agent with good activity. It has been further discovered that the formed narrow range ethoxylates possess better surface-active properties when compared with the broad distribution range adducts. Also, the narrow range ethoxylates seem to act faster and have a better detergent activity than the broad distribution adducts; this faster germicidal and detergent activity does not correlate with what is expected of non-ionic ethoxylates. Generally, non-ionic ethoxylates such as TWEEN 80 and SPAN 20. are not only germicidally inactive but the former is routinely used to stop germicidal action of chemicals. While not intending to be bound by theory, it appears that controlled ethoxylation or propoxylation adds to available hydroxyl radicals by ring cleavage with regeneration of the hydroxyl group. This reaction is an addition reaction without termination. Such ethoxylation is discussed in more detail in Dillan, K., *Effects of the Ethylene Oxide Distribution of Nonionic Surfactant Properties,* JAOCS, Vol. 62, Pgs. 1144–1151, 1985, which is herein incorporated by reference.

The glyceryl fatty acid ester which is to be ethoxylated or propoxylated in the practice of the present invention is selected from the group consisting of polyhydric alcohols, polyglycerols, sucrose, glucose, sorbitol, propylenediol and glyceryl fatty acid esters having about six to about twenty-one carbon atoms. The preferred compounds include monocaprylin, monocaprin, monolaurin, monamyristin, monopalmitolein, α-monopalmitin, monostearin, monoolein, 1-monolinolein, 1-monolinolenin, and mixtures thereof. Still more preferred are monocaprylin, monocaprin, monolaurin, monomyristin, monopalmitolein, monoolein, monoicosenin and monoerucin and mixtures thereof. The highly preferred compounds are monocaprylin, monocaprin and monolaurin and mixtures thereof.

The glyceryl fatty acid esters are ethoxylated or propoxylated by conventional ethoxylating or propoxylating compounds. The compounds are preferably selected from the group consisting of ethylene oxide, propylene oxide, mixtures thereof, and similar ringed compounds which provide a material which is effective. Most preferably, the ethoxylation compound is selected from the group consisting of ethylene oxide, propylene oxide and mixtures thereof. Mnolaurin is the most preferred.

The glyceryl fatty acid esters are ethoxylated or propoxylated under conventional controlled conditions and techniques to a narrow range according to conventional methods, such as those in the Dillan article, further incorporated by reference. The glyceryl fatty acid esters are ethoxylated or propoxylated by a suitable amount of ethoxylate or propoxylate compound. In a preferred embodiment, the ethoxylation or propoxylation compound is reacted at a level of about 0.5 to about 20 moles, more preferably, at about 0.5to about 3.0 moles and, highly preferred, at about 0.5 to about 1.0 moles per mole of the glyceryl ester.

The ethoxylation or propoxylation adds at least one-quarter, and preferably at least about one-half or more ethoxy or propoxy units per glyceryl fatty acid ester unit. Preferably 0.5 to 6.0, more preferably 0.5 to 3.0 and, still more preferably, 0.5 to 1.0 ethoxy or propoxy units are added per glyceryl fatty acid ester.

Generally, the adduct formed by the reaction of the glyceryl fatty acid ester and ethoxylation or propoxylation compound occurs as described. However, it is noted that the reaction products are complex and may be formed by other well known conventional processes in the chemical art. For example, the ethoxylation of a mixture of glycerol and fatty acids, may yield the same useful products.

The glyceryl fatty acid esters (both ethoxylated/propoxylated and non-ethoxylated/propoxylated), first fatty acid, and second fatty acid may be directly added or admixed with the food composition, cosmetics, drugs, or the like during the manufacturing process. However, conventional food-grade carriers may be employed when an additive composition is prepared. Food grade carriers selected from the group consisting of alcohols, propylene glycol, phenoxyethanol, ethanol, and mixtures thereof may be employed in such additive compositions. Preferred carriers include propylene glycol, ethanol, and mixtures thereof. These carriers enhance the mixing of the elements.

Water may also be used q.s. to form the remainder of the carrier and may be selected from the group consisting of distilled water, dionized water, tap and well water.

The alcohols are employed in the compositions of the present invention at any suitable level. In a preferred embodiment they are present at a level of about 5 to 60%, more preferred at about 10 to 30% and, highly preferred, at about 20 to 25% weight per volume of solution.

Water is employed in solution as the remainder of the solution.

EXAMPLE 1

The following formula has been found to be active against a group of organism when added to a food composition.

| | |
|---|---|
| Glycerol Monolaurin | .05–.5% |
| Caprylic Acid/Capric Acid Mixture | .05–.5% |
| Propylene glycol | 10–30% |
| Water | 69–89.9% |

The above formula is effective against yeasts, fungii, gram negative and gram positive organism.

The critical components of the compositions of the present invention are added individually (glyceryl ester; first fatty acid; second fatty acid) directly into the food composition, cosmetics, drugs, or the like during the manufacturing processing in any convenient order. After addition of the components, the substances are mixed thoroughly so as to uniformly distribute the composition throughout the substance. Once the composition is uniformly distributed in the substance, the substance will be enhanced with antimicrobial properties. However, a composition of the present invention may be prepared as an additive composition prior to addition to the final preserved food, cosmetic, drug, etc. The additive is then added directly to the food, drug or the like.

EXAMPLE 2

A powder cheddar cheese was supplied by SeaFla, Inc. 2.5% grams of the powder cheddar cheese was mixed with 10 ml of tap water at about 23° C. The resulting mixture had a smooth consistency. The following components were added and mixed into the cheese sauce in the concentrations as listed in Table 1 to form a preserved food composition according to the present invention.

TABLE 1

|  | % Concentration with Respect to Total Gram Weight of the Mixture |
| --- | --- |
| 3 parts Glycerol Monolaurin | .05–.5% |
| 7 parts Caprylic Acid/Capric Acid Mixture (6:4) | .05–.5% |

The following organisms were identified in the cheese sauce at the conception of the experiment; Leuconostoc, Staphlococcus, Lactobacillus, Bacillus. (all gram positive) and Mucor (a fungus). These organisms were present at a level of approximately $2.0 \times 10^3$ colony forming units/gram (CFU/gram) in all samples.

Several cheese sauce samples were incubated at roam temperature, while other samples were incubated at approximately 37° C., both were checked daily for spoilage.

A control sample not of the present invention spoiled in 8 days (at room temperature) and 5 days (at elevated temperatures 37° C.). The sauce was considered to be spoiled when CFU/gram=$Log_{10}$ 5–6 CFU/gram. Table 2 contains the results of the samples tested.

TABLE 2

Effect On Shelf-Life Of A Cheese Sauce

| Concentration of Glycerol Monolaurin & $C_8/C_{10}$ Fatty Acid With Respect Total Gram Weight of the Mixture | Number of Days Before Spoilage Occurred at Specified Incubation the Temperatures | |
| --- | --- | --- |
| | Room Temperature | 37° C. |
| 0.0% | 8 days | 5 days |
| .05% | 34 days | 34 days |
| .10% | 34 days | 34 days |
| .20% | >6 weeks | >6 weeks |

The experiment was stopped after 7 weeks and the samples having 0.20% concentrations were considered preservative up to this point.

While the above summarizes the present invention, it will became apparent to those skilled in the art that modifications, variations and alterations may be made without deviating from the scope and spirit of the present invention as described and claimed herein.

What is claimed is:

1. An antimicrobial preservative or additive composition comprising a safe and effective amount of a mixture comprising:

(a) a glycerol monoester of lauric acid present in an amount of about 0.025 to about 3.0 percent by weight of the composition;

(b) a binary mixture of fatty acids comprising:
        (i) a first fatty acid comprising capric acid, and
        (ii) a second fatty acid comprising caprylic acid; wherein (i) and (ii) are present in weight:weight ratio of about 4:6; and (c) a carrier which optionally includes a chelating agent, wherein said composition is added to a final product at a level of about 0.05 to about 0.20%.

2. A composition according to claim 1 wherein said monoester is present at a level of about 0.025 to about 1 percent of the composition.

3. A composition according to claim 1 wherein said monoester is present at a level of about 0.05 to about 0.5 percent of the composition.

4. A composition according to claim 1 wherein said carrier comprises at least one component selected from the group consisting of alcohols, water, and mixtures thereof.

5. A composition according to claim 1 wherein the carrier comprises an alcohol selected from the group consisting of propylene glycol, phenoxyethanol, ethanol, and mixture thereof.

6. A composition according to claim 1 wherein the carrier additionally comprises a food-grade surfactant.

7. A shelf-stable food composition comprising a food stuff employing a safe and effective amount of a preservative composition comprising:

(a) a glycerol monoester of lauric acid; and (b) a binary mixture of fatty acids comprising:
        (i) a first fatty acid comprising capric acid;
        (ii) a second fatty acid comprising caprylic acid; wherein (i) and (ii) are present in a weight:weight ratio of about 4:6 wherein said composition is added to a final product at a level of about 0.05 to about 0.20%.

8. A composition according to claim 7 wherein (a):(b) are present in a weight:weight ratio of about 1:10 to about 10:1.

9. A method of preserving a food, drug, cosmetic or other composition in need of preservation or improved shelf-life comprising the step of adding to said composition in need of preservation or improved shelf life a safe and effective amount of a composition according to claim 1.

10. A composition according to claim 1 wherein said carrier includes a chelating agent, said chelating agent being selected from the group consisting of lactic acid and its salts, polyphosphoric acid and its salts, EDTA, $EDTA(Na)_2$, $EDTA(Na)_4$, citric acid and its salts and mixtures thereof.

11. A composition according to claim 1 wherein the glycerol ester has been ethoxylated or propoxylated at a level of at least about 0.5 to about 20 moles of ethoxylate or propoxylate per mole of glycerol ester.

* * * * *

UNITED STATES PATENT AND TRADEMARK OFFICE
CERTIFICATE OF CORRECTION

PATENT NO. : 6,638,978 B1
DATED : October 28, 2003
INVENTOR(S) : Jon J. Kabara

It is certified that error appears in the above-identified patent and that said Letters Patent is hereby corrected as shown below:

Column 2,
Line 57, "Weirii" should be italicized.

Column 5,
Line 41, after "20" delete ".".

Column 6,
Lines 5-6, "Mnolaurin" should be -- Monolaurin --.
Linme 16, "0.5to" should be -- 0.5 to --.

Column 7,
Line 39, "roam" should be -- room --.

Column 8,
Lines 20 and 47, after the phrase "to about 0.20%" insert -- thereby providing a synergestically stable and antimicrobial composition --.

Signed and Sealed this

Eighth Day of June, 2004

JON W. DUDAS
*Acting Director of the United States Patent and Trademark Office*